(12) United States Patent
Yang et al.

(10) Patent No.: US 11,986,230 B2
(45) Date of Patent: May 21, 2024

(54) FLEXIBLE CRYOABLATION NEEDLE DEVICE RESISTANT TO LOW TEMPERATURE AND HIGH PRESSURE

(71) Applicant: ACCU TARGET MEDIPHARMA (SHANGHAI) Co., Ltd., Shanghai (CN)

(72) Inventors: Chi Yang, Shanghai (CN); Binkai Xu, Shanghai (CN); Yinlong Wu, Shanghai (CN); Rui Zhang, Shanghai (CN)

(73) Assignee: ACCU TARGET MEDIPHARM (SHANGHAI) CO., LTD., Shanghai (CN)

( * ) Notice: Subject to any disclaimer, the term of this patent is extended or adjusted under 35 U.S.C. 154(b) by 485 days.

(21) Appl. No.: 17/311,802

(22) PCT Filed: Mar. 7, 2019

(86) PCT No.: PCT/CN2019/077262
§ 371 (c)(1),
(2) Date: Jun. 8, 2021

(87) PCT Pub. No.: WO2020/155301
PCT Pub. Date: Aug. 6, 2020

(65) Prior Publication Data
US 2022/0015815 A1 Jan. 20, 2022

(30) Foreign Application Priority Data
Jan. 28, 2019 (CN) .......................... 201910077358.7

(51) Int. Cl.
*A61B 18/02* (2006.01)
*A61B 18/00* (2006.01)

(52) U.S. Cl.
CPC .... *A61B 18/02* (2013.01); *A61B 2018/00172* (2013.01); *A61B 2018/00601* (2013.01);
(Continued)

(58) Field of Classification Search
CPC .......... A61B 18/02; A61B 2018/00172; A61B 2018/0262; A61B 2018/0293; A61B 2018/0212
See application file for complete search history.

(56) References Cited

U.S. PATENT DOCUMENTS

5,423,807 A * 6/1995 Milder .............. A61M 25/0158
607/105
6,014,864 A * 1/2000 Owen .................... F28F 13/00
62/51.1
(Continued)

*Primary Examiner* — Daniel W Fowler
(74) *Attorney, Agent, or Firm* — NZ CARR LAW OFFICE (57) ABSTRACT

The disclosure provides a flexible cryoablation needle device resistant to a low temperature and a high pressure, a threaded part is arranged on the outer wall of a liner pipe to enhance a connection strength between the liner pipe and a flexible pipe structure. Since an annular protrusion portion is arranged on the outer wall of the liner pipe, further leakage of a gas coming from a pressure relief process is prevented and the connection strength is enhanced as well. Air tightness and connection strength are further guaranteed by radial extrusion of extruding pipes. And an inner cavity in a cutter head is directly subjected to pressure relief through a cutter head vent, a pressure relief intermediate cavity, a liner vent, a flexible pipe vent and a pressure relief gap.

20 Claims, 2 Drawing Sheets

(52) U.S. Cl.
CPC ............... *A61B 2018/0063* (2013.01); *A61B 2018/0293* (2013.01)

(56) References Cited

U.S. PATENT DOCUMENTS

| | | | |
|---|---|---|---|
| 9,872,718 B2 * | 1/2018 | Nash | A61M 25/1006 |
| 2003/0199861 A1 * | 10/2003 | Lafontaine | A61B 18/02 606/21 |
| 2011/0054453 A1 * | 3/2011 | Lalonde | A61B 18/02 606/22 |
| 2014/0276711 A1 * | 9/2014 | Duong | A61B 18/02 606/25 |
| 2015/0300569 A1 * | 10/2015 | Baust | F17C 1/00 62/50.1 |

* cited by examiner

FLEXIBLE CRYOABLATION NEEDLE DEVICE RESISTANT TO LOW TEMPERATURE AND HIGH PRESSURE

TECHNICAL FIELD

The present disclosure relates to the field of medical treatment, and in particular to a flexible cryoablation needle device resistant to a low temperature and a high pressure.

BACKGROUND

A flexible cryoscalpel is applied to biopsy, foreign body extraction, cryo-cutting, ablation inactivation, etc. in a natural cavity (such as the bronchus) of a human body. Generally, it includes five major members, namely a cutter head, a flexible catheter, a handle, an extension pipe and a quick connector.

A conventional cryoscalpel can be applied to biopsy, foreign body extraction, and cryo-cutting. A carbon dioxide or a nitrous oxide is taken as a gas source, where a gas input working pressure is up to 900 psi, a cutter head is at a temperature of −40° C. to −80° C., and a back pressure in the cutter head is generally lower than 100 psi under a normal working condition. The flexible catheter is a single-layer pipe, and it requires no thermal insulation treatment as the temperature is not low.

Taking a flexible cryoscalpel for tumor ablation as an example, it is a high-pressure and low-temperature treatment apparatus, of which a gas input working pressure is about 1500 psi, a cutter head is at a temperature of −140° C. to −170° C., and a back pressure in the cutter head is 300 psi to 500 psi under a normal working condition. Therefore, such a low-temperature and high-pressure environment requires extremely high connection strength and tightness between a metal cutter head and a plastic flexible catheter. If the cutter head is disconnected from the flexible catheter, the cutter head will rush out to pierce human tissues and cause gas leakage as well, which will result in additional freezing injuries or gas embolism. Additional freezing injuries or gas embolism may also be caused by gas leakage due to insufficient connection tightness of the cutter head and the flexible catheter. In addition, the flexible cryoscalpel for tumor ablation may cause freezing injuries to a normal cavity wall of a human body due to a quite low temperature.

Still taking a flexible cryoscalpel for tumor ablation as an example, if a gas return pipeline thereof is blocked (such as ice blocking), a back pressure in a cutter head may be as high as 1500 psi, and a plastic flexible catheter cannot bear such a high pressure and will burst; and if the catheter bursts during an operation, a great amount of gas will be leaked to a natural cavity, which may endanger a patient's life.

It can be seen that an existing flexible cryoscalpel in the related art has the following defects: the connection strength and air tightness of a cutter head and a flexible catheter are insufficient, and the catheter bursts easily when the cutter head has an extremely high pressure.

SUMMARY

The present disclosure provides a flexible cryoablation needle device resistant to a low temperature and a high pressure to solve the problem that a catheter bursts easily when a cutter head has an extremely high pressure by automatic pressure relief. Moreover, the connection strength and air tightness of a flexible catheter and a cutter head are effectively improved by virtue of a threaded part, an annular protrusion portion and a first extruding pipe.

According to a first aspect of the present disclosure, a flexible cryoablation needle device resistant to a low temperature and a high pressure is provided and includes: a cutter head structure and a flexible pipe structure which is connected to the rear end of the cutter head structure; the cutter head structure is provided with an inner cavity; the cutter head structure includes a cutter head front section and a cutter head rear section; the front end of the cutter head rear section is connected to the rear end of the cutter head front section; the cutter head rear section has a smaller outer diameter than the cutter head front section; the flexible cryoablation needle device further includes a liner pipe, a flexible pipe structure, a pressure relief assembly, a pressure relief intermediate cavity and a first extruding pipe; the flexible pipe structure is provided with a pressure relief gap and a flexible pipe vent; the rear end face of the cutter head front section is provided with a cutter head vent; the liner pipe is provided with a liner vent;

the front end of the liner pipe is connected with the rear end face of the cutter head front section; the pressure relief intermediate cavity is formed between the inner side of the liner pipe and the outer side of the cutter head rear section along the radial direction of the cutter head structure; the pressure relief intermediate cavity is formed between the rear end face of the cutter head front section and a fixing part and along the axial direction of the cutter head structure; the fixing part is connected between the outer side of the cutter head rear section and the inner side of the liner pipe; the flexible pipe structure is arranged on the outer side of the liner pipe along the radial direction of the cutter head structure; the pressure relief intermediate cavity communicates with the pressure relief gap through the liner vent and the flexible pipe vent; the inner cavity is connected to one side of the cutter head vent; the pressure relief intermediate cavity is connected to the other side of the cutter head vent;

at least a part of the outer wall of the liner pipe is attached to the inner wall of the flexible pipe structure; the outer wall, attached to the flexible pipe structure, of the liner pipe is provided with a concave-convex structure; the first extruding pipe is sleeved outside the flexible pipe structure and is located on the outer side of a part of the concave-convex structure; the concave-convex structure includes a threaded portion and/or an annular protrusion portion; and the pressure relief assembly is arranged in the pressure relief intermediate cavity to close the cutter head vent when a pressure in the inner cavity is lower than a pressure threshold and control the cutter head vent, the flexible pipe vent and the liner vent to communicate with one another when the pressure in the inner cavity is higher than or equal to the pressure threshold, such that a gas in the cutter head structure is exhausted to relieve the pressure through the cutter head vent, the pressure relief intermediate cavity, the liner vent, the flexible pipe vent and the pressure relief gap in sequence.

Optionally, the pressure relief assembly may include a slider and a spring which are located in the pressure relief intermediate cavity; the spring is connected with the slider and the fixing part along the axial direction of the cutter head structure; a first sealing member is arranged on one side of the rear end face of the cutter head front section;

the spring is configured to cause the first sealing member to be driven by an elastic force and clamped by the slider and the rear end face of the cutter head front section when a pressure in the inner cavity is lower than a pressure threshold so as to close the cutter head vent, and the spring is compressed by the pressure in the inner cavity when the pressure in the inner cavity is higher than or equal to the pressure threshold such that the cutter head vent is not closed; and the closure mentioned above includes both direct closure and indirect closure, and the indirect closure can be understood as preventing circulation under a non-contact condition.

Optionally, the first sealing member is connected with the front end of the slider; the cutter head vent may be directly closed by the first sealing member when the first sealing member is clamped by the slider and the rear end face of the cutter head front section; and when the spring is compressed by the pressure in the inner cavity, the first sealing member is separated from the cutter head vent, such that the cutter head vent is not closed.

Optionally, the first sealing member is connected with the rear end face of the cutter head front section; the first side, along the radial direction of the cutter head structure, of the slider may be provided with a middle gap; the pressure relief intermediate cavity includes a first pressure relief sub-cavity located and a second pressure relief sub-cavity, wherein the first pressure relief sub-cavity is located on one side of the front end of the slider, and the second pressure relief sub-cavity is located on one side of the rear end of the slider;

the front end of the middle gap is closed by the first sealing member when the first sealing member is clamped by the slider and the rear end face of the cutter head front section, such that the first pressure relief sub-cavity is isolated from the second pressure relief sub-cavity; and when the spring is compressed by the pressure in the inner cavity, the cutter head vent, the first pressure relief sub-cavity, the middle gap, the second pressure relief sub-cavity, the flexible pipe vent and the pressure relief gap communicate with one another in sequence.

Optionally, the second side, along the radial direction of the cutter head structure, of the slider may be provided with a second sealing member, and the second sealing member is configured to isolate the first pressure relief sub-cavity from the second pressure relief sub-cavity on the second side of the slider.

Optionally, the second side of the slider may be provided with a groove, and the second sealing member is installed in the groove.

Optionally, both the first sealing member and the second sealing member may be sealing rings.

Optionally, the flexible pipe structure may include a flexible inner catheter and a flexible outer catheter which is arranged outside the flexible inner catheter; the flexible outer catheter may include a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

Optionally, the material of the flexible inner catheter and the flexible outer catheter is poly tetra fluoroethylene(PTFE).

Optionally, the flexible cryoablation needle device may further include a second extruding pipe, and the second extruding pipe is sleeved outside the flexible inner catheter and is located on the outer side of the concave-convex structure.

Optionally, the device may further include a pipeline structure; the pipeline structure penetrates into the cutter head rear section along the axial direction of the cutter head structure; an entry channel is formed in the pipeline structure to allow a gas to enter into the inner cavity; and a gas return channel is formed between the inner side of the cutter head rear section and the outer side of the channel structure to allow the gas in the inner cavity to exhaust to one side of the rear end of the cutter head rear section.

According to the flexible cryoablation needle device provided by the present disclosure, the threaded part arranged on the outer wall of the liner pipe can enhance the connection strength between the liner pipe and the flexible pipe structure. Since the outer wall of the liner pipe is provided with the annular protrusion portion, further leakage of a gas coming from a pressure relief process is prevented, and the connection strength is enhanced as well. According to the flexible cryoablation needle device provided by the present disclosure, air tightness and connection strength are further guaranteed by radial extrusion of an extruding pipe.

Also, according to the flexible cryoablation needle device provided by the present disclosure, the inner cavity in the cutter head is directly subjected to pressure relief through the cutter head vent, the pressure relief intermediate cavity, the liner vent, the flexible pipe vent and the pressure relief gap, wherein when a pressure in the inner cavity is higher than or equal to a pressure threshold, pressure relief can be automatically controlled to avoid occurrence of an extremely high pressure in the cutter head, thereby avoiding burst of a catheter.

The present disclosure is also different from a solution of directly arranging pressure relief related members in a gas return channel. If the pressure relief related members are directly arranged in the gas return channel, automatic pressure relief is only realized when the gas return channel is blocked. If a gas return channel of a flexible cryoscalpel is blocked, a positive pressure relief function cannot be achieved. However, based on actual experiments and studies on blocking phenomena during use, it is found in the present disclosure that in actual situations, blocking may occur at any other position, such as a flexible catheter of a flexible cryoscalpel, an extension pipe section, etc.; therefore, the present disclosure realizes direct pressure relief of a cutter head, thereby effectively responding to a variety of blocking conditions and conveniently responding to a situation about an extremely high pressure in a cutter head caused by various reasons.

In the related existing art, in order to realize automatic pressure relief, a general idea is to realize automatic pressure relief through the combination of a pressure sensor and a solenoid valve. In an optional solution of the present disclosure, under a specific condition that the space is limited, a flexible cryoscalpel uses the motion modes of the slider, the sealing members and the spring for reference, and thus automatic pressure is realized with a simpler structure, a lower cost and less space use.

In an optional solution of the present disclosure, a double-layered pipe structure including a flexible inner catheter and a flexible outer catheter is used to facilitate heat insulation and prevent injuries of a human body caused by a low temperature of a flexible cryoscalpel. Also, a heat insulation effect can be further improved during pressure relief by generation of a pressure relief gap and/or vacuumizing of the pressure relief gap.

In addition, in view of the situation that a rubber or plastic material in the related existing art may be embrittled at a low temperature, an optional solution of the present disclosure uses a tetrafluoroethylene material. With a good mechanical toughness, a tetrafluoroethylene material can maintain an elongation of 5% even when a temperature drops to −196° C. Therefore, safe sealing under a low temperature can be realized by adopting tetrafluoroethylene for manufacturing inner and outer layers of flexible catheters.

BRIEF DESCRIPTION OF THE DRAWINGS

In order to describe the technical solutions in an embodiment of the present disclosure or in the existing art more clearly, drawings required in the description of the embodiment or the existing art will be briefly described. Apparently, the drawings described below are merely some embodiments of the present disclosure, and other drawings can also be obtained based on these drawings by those of ordinary skill in the art without any creative work.

REFERENCE SIGNS

1—cutter head structure;
11—cutter head front section;
12—cutter head rear section;
13—cutter head vent;
14—inner cavity;
2—flexible pipe structure;
21—flexible pipe vent;
22—pressure relief gap;
23—flexible inner catheter;
24—flexible outer catheter;
241—first outer catheter section;
242—second outer catheter section;
3—pressure relief intermediate cavity;
4—pressure relief assembly;
41—slider;
42—spring;
43—first sealing member;
44—second sealing member;
5—liner pipe;
51—liner vent;
52—threaded part;
53—annular protrusion portion;
54—welding point;
6—first extruding pipe;
7—pipeline structure;
8—second extruding pipe; and
9—fixing part.

DETAILED DESCRIPTION

Technical solutions in the examples of the present invention will be clearly and completely described below in conjunction with the drawings in the examples of the present invention. Apparently, the examples described are merely some examples rather than all examples of the present invention. Based on the examples of the present invention, all other examples obtained by those skilled in the art without any creative efforts shall fall within the protection scope of the present invention.

In the description, the claims and the drawings of the present invention, the terms "first", "second", "third", "fourth", etc. (if existing) are used for distinguishing similar objects rather than describing a specific order or sequence. It should be understood that the data used in this way may be interchanged under appropriate circumstances so that the examples of the present invention described herein may be implemented in an order other than those illustrated or described herein. In addition, the terms "including" and "comprising" and any variations thereof are intended to cover non-exclusive inclusions. For example, a process, method, system, product, or device that includes a series of steps or units is not necessarily limited to those clearly listed steps or unit, but may also include other steps or unit that are not clearly listed or are inherent to the process, method, product, or device.

The technical solutions of the present invention will be described in detail below with specific examples. The following specific examples may be combined with each other, and the same or similar concepts or processes may not be repeated in some examples.

Figure 1:
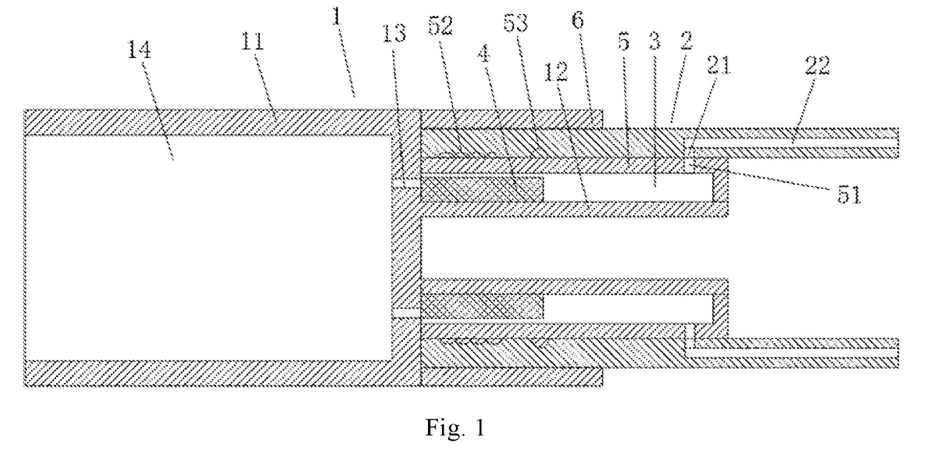
FIG. 1 is a structure diagram of a flexible cryoablation needle device resistant to a low temperature and a high pressure in one embodiment of the present disclosure.

FIG. 1 is a structure diagram of a flexible cryoablation needle device resistant to a low temperature and a high pressure in one embodiment of the present disclosure.

Referring to FIG. 1, a flexible cryoablation needle device resistant to a low temperature and a high pressure includes: a cutter head structure 1 and a flexible pipe structure 2 connected to the rear end of the cutter head structure 1, wherein the cutter head structure 1 is provided with an inner cavity 14 and includes a cutter head front section 11 and a cutter head rear section 12; the front end of the cutter head rear section 12 is connected to the rear end of the cutter head front section 11; the cutter head rear section 12 has a smaller outer diameter than the cutter head front section 11; the flexible cryoablation needle device further includes a liner pipe 5, a pressure relief assembly 4, a pressure relief intermediate cavity 3 and a first extruding pipe 6.

The flexible pipe structure 2 is provided with a pressure relief gap 22 and a flexible pipe vent 21; the rear end face of the cutter head front section 11 is provided with a cutter head vent 13; the liner pipe 5 is provided with a liner vent 51;

The front end of the liner pipe 5 is connected with the rear end face of the cutter head front section 11; the pressure relief intermediate cavity 3 is formed between the inner side of the liner pipe 5 and the outer side of the cutter head rear section 12 and along the radial direction of the cutter head structure 1; the pressure relief intermediate cavity 3 is formed between the rear end face of the cutter head front section 11 and a fixing part 9 and along the axial direction of the cutter head structure 1; the fixing part 9 is connected between the outer side of the cutter head rear section 12 and the inner side of the liner pipe 5; the flexible pipe structure 2 is arranged on the outer side of the liner pipe 5 and along the radial direction of the cutter head structure 1; the pressure relief intermediate cavity 3 communicates with the pressure relief gap 22 through the liner vent 51 and the flexible pipe vent 21; the inner cavity 14 is connected to one side of the cutter head vent 13, wherein the side is the left side of the cutter head vent 13 shown in FIG. 1; the pressure relief intermediate cavity 3 is connected to the other side of the cutter head vent, wherein the other side is the right side of the cutter head vent 13 shown in FIG. 1; in addition, the pressure relief intermediate cavity 3 can be connected to one side of the flexible pipe vent 21 through the liner vent 51, wherein the side is the lower side of the flexible pipe vent 21 shown in FIG. 1; and also the flexible pipe vent 21 is formed along the radial direction of the cutter head structure.

Wherein, the two sides of the cutter head vent 13 and the flexible pipe vent 21 may not limited to the radial and axial directions shown in FIG. 1. For example, the cutter head vent 13 may be in the axial direction or in the radial direction; and the flexible pipe vent 21 and the liner vent 51 may be in the radial direction or in the axial direction. In addition, there may be one or more cutter head vents 13, flexible pipe vents 21, and liner vents 51. If there are more than one, the plurality of cutter head vents may be distributed around the axial direction of the cutter head structure 1, and the plurality of flexible pipe vents 21 and liner vents 51 may be distributed around the axial direction of the cutter head structure.

Wherein, the pressure relief gap 22 may be a ring-shaped gap, or it may include a plurality of gap portions which may be distributed around the axial direction of the cutter head structure 1.

If the pressure relief gap 22 includes a plurality of gap portions and there are a plurality of flexible pipe vents 21 and a plurality of liner vents 51, each gap portion can be connected with at least one flexible pipe vent 21.

In addition, the above-mentioned vents may be verified in shape, and is not limited to a cylindrical hole structure. For example, a hole structure may be in a shape with a large end and a small end. For another example, the section of the hole structure may be circular or polygonal.

The pressure relief assembly 4 is arranged in the pressure relief intermediate cavity 3 and configured to close the cutter head vent 13 when a pressure in the inner cavity 14 is lower than a pressure threshold, and control the cutter head vent 13, the flexible pipe vent 21 and the liner vent 51 to communicate with one another, such that a gas in the cutter head structure 1 can be exhausted to relieve the pressure through the cutter head vent 13, the pressure relief intermediate cavity 3, the liner vent 51, the flexible pipe vent 21 and the pressure relief gap 22 in sequence.

The above-mentioned closure may be any means that prevents circulation on both sides of the vents.

The above-mentioned controlling the cutter head vent 13, the flexible pipe vent 21 and the liner vent 51 to communicate with one another may be understood as that, the cutter head vent 13, the liner vent 51 and the flexible pipe vent 21 communicate with one another; specifically, based on differences of the vents to be closed, an implemented automatic control process may also be adaptively changed; for example, if only the cutter head vent 13 is closed, and the flexible pipe vent 21 and the liner vent 51 are not closed, the implemented automatic control may include controlling the cutter head vent 13 to not be closed; for another example, if only the flexible pipe vent 21 and the liner vent 51 are closed and the cutter head vent 13 is not closed, the implemented automatic control may include controlling the flexible pipe vent 21 and the liner vent to not be closed; and for a further example, if the cutter head vent 13 and the flexible pipe vent 21 are both closed, the implemented automatic control may include controlling the cutter head vent 13 and the flexible pipe vent 21 not to be closed. In addition, the closure mentioned above includes both direct closure and indirect closure, and the indirect closure can be understood as preventing circulation under a non-contact condition.

According to the flexible cryoablation needle device resistant to a low temperature and a high pressure provided by this embodiment, the inner cavity in the cutter head is directly subjected to pressure relief through the cutter head vent, the pressure relief intermediate cavity, the liner vent, the flexible pipe vent and the pressure relief gap, wherein when a pressure in the inner cavity is higher than or equal to a pressure threshold, pressure relief can be automatically controlled to avoid occurrence of an extremely high pressure in the cutter head, thereby avoiding burst of a catheter.

Also, this embodiment is also different from a solution of directly arranging pressure relief related members in a gas return channel. If the pressure relief related members are directly arranged in the gas return channel, automatic pressure relief is only realized when the gas return channel is blocked. If a gas return channel of a flexible cryoscalpel is blocked, a positive pressure relief function cannot be achieved. However, based on actual experiments and studies on blocking phenomena during use, it is found in this embodiment that in actual situations, blocking may occur at any other position, such as a flexible catheter of a flexible cryoscalpel, an extension pipe section, etc.; therefore, this embodiment realizes direct pressure relief of a cutter head, thereby effectively responding to a variety of blocking conditions and conveniently responding to a situation about an extremely high pressure in a cutter head caused by various reasons.

Figure 2:
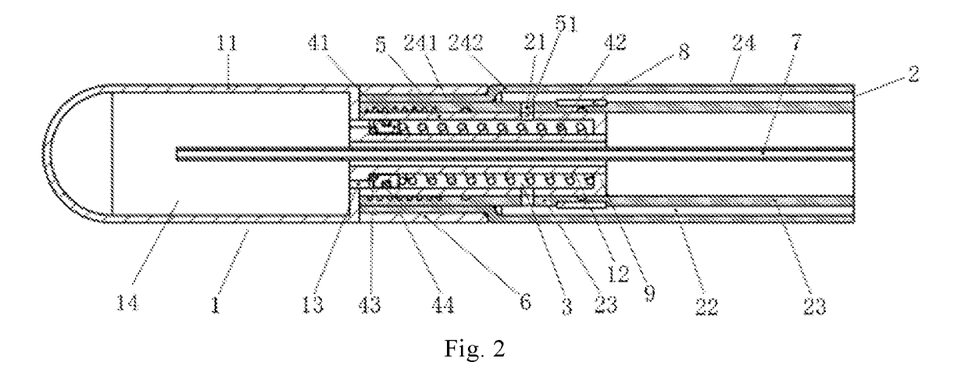
FIG. 2 is a structure diagram I of a flexible cryoablation needle device resistant to a low temperature and a high pressure in another embodiment of the present disclosure.
Figure 3:
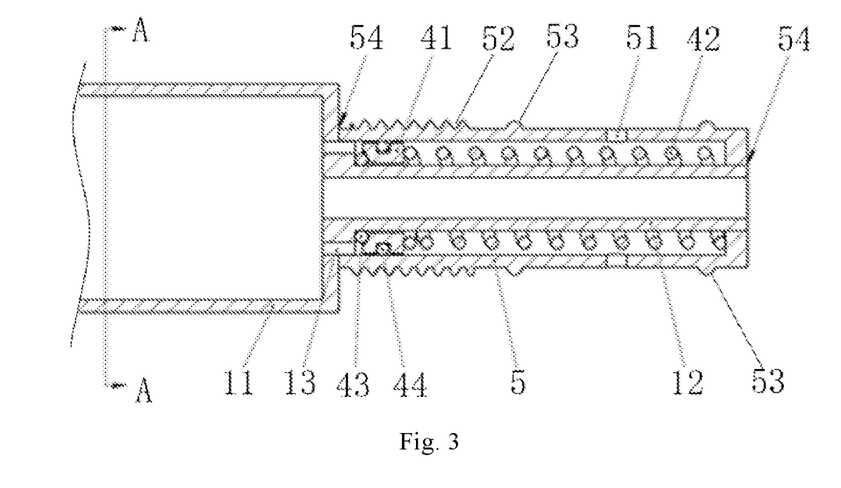
FIG. 3 is a partial structure diagram I of a flexible cryoablation needle device resistant to a low temperature and a high pressure in another embodiment of the present disclosure.
Figure 4:
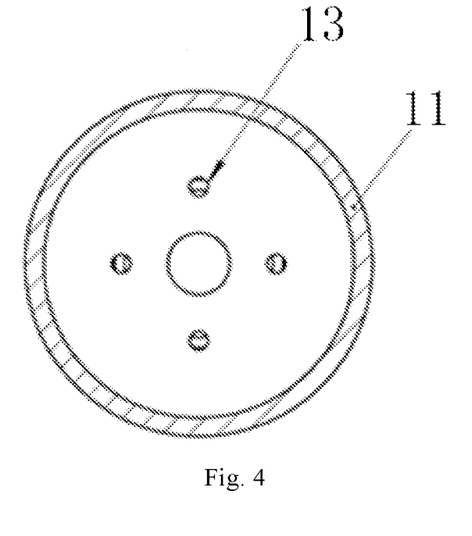
FIG. 4 is a structure diagram of an A-A section in FIG. 3.
Figure 5:
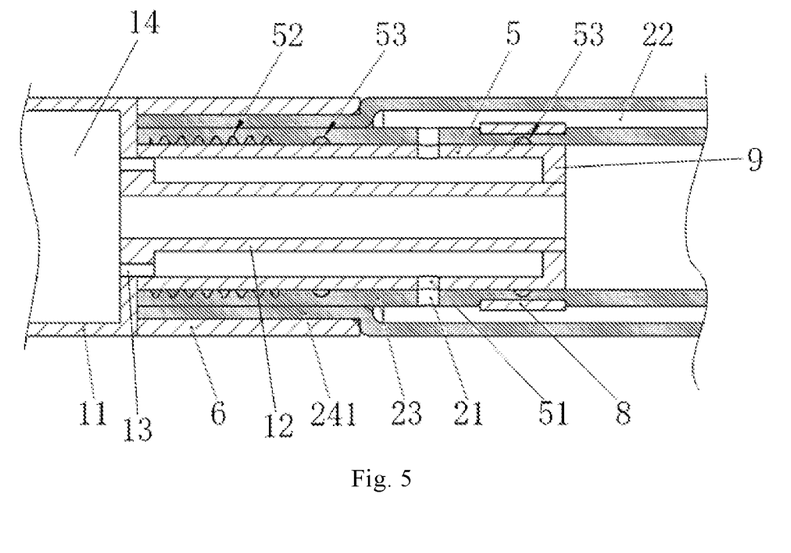
FIG. 5 is a structure diagram II of a flexible cryoablation needle device resistant to a low temperature and a high pressure in another embodiment of the present disclosure.

FIG. 2 is a structure diagram I of a flexible cryoablation needle device resistant to a low temperature and a high pressure in another embodiment of the present disclosure; FIG. 3 is a partial structure diagram I of a flexible cryoablation needle device resistant to a low temperature and a high pressure in another embodiment of the present disclosure; FIG. 4 is a structure view of an A-A section in FIG. 3; and FIG. 5 is a partial structure diagram II of a flexible cryoablation needle device resistant to a low temperature and a high pressure in another embodiment of the present disclosure.

Referring to FIG. 2 to FIG. 5, the cutter head structure 5 includes a cutter head front section 11 and a cutter head rear section 12; the front end of the cutter head rear section 12 is connected to the rear end of the cutter head front section 11; the cutter head rear section 12 has a smaller outer diameter than the cutter head front section 11; the cutter head vent 13 is formed in the rear end face of the cutter head front section 11 and located on the outer side of the cutter head rear section 12; and the pressure relief intermediate cavity 3 is located on one side of the rear end of the cutter head front section 11.

The cutter head structure 1 can be adaptively connected with the flexible pipe structure 2 by its dimensional changes, so as to guarantee uniform matching of the overall dimensions.

Referring to FIG. 2 and FIG. 3, the pressure relief assembly 4 includes a slider 41 and a spring 42 which are located in the pressure relief intermediate cavity 3; the fixing part 9 may be a part of the liner pipe 5 or is integrally formed with the liner pipe 5; the spring 42 is connected with the slider 41 and the fixing part 9 along the axial direction of the cutter head structure 1; and a first sealing member 43 is arranged on one side of the rear end face of the cutter head front section 11. In an example, the spring 42 may be formed in a way of being wound around the outer side of the cutter head rear section 12, and connected with the fixing part 9 and the slider 41.

The spring 42 may be configured to drive the first sealing member 43 to be clamped by the slider 41 and the rear end face of the cutter head front section 11 by an elastic force when a pressure in the inner cavity 14 is lower than a pressure threshold so as to close the cutter head vent 13. Specifically, when the pressure is lower than the pressure threshold, the spring 42 may be compressed to generate the above-mentioned elastic force.

The spring 42 may be compressed by the pressure in the inner cavity 14 when the pressure in the inner cavity 14 is higher than or equal to the pressure threshold to ensure that the cutter head vent 13 is not closed. Specifically, when the pressure is lower than the pressure threshold, the spring 42 may be compressed to a certain extent or be further compressed when the pressure is higher than or equal to the pressure threshold.

It can be seen that the above-mentioned configuration can be understood as the adaptation of a deformation capacity and a length of the spring 42 and the pressure relief intermediate cavity 3 to achieve the above functions. Also, the pressure threshold may be any numerical value adjusted according to specific situations, and the numerical value can be adjusted and determined by type selection as well as manufacturing, formation and installation processes of the spring 42.

In a specific implementation process, the first sealing member 43 is connected with the front end of the slider 41; the cutter head vent 13 can be closed by the first sealing member 43 when the first sealing member 43 is clamped by the slider 41 and the rear end face of the cutter head front section 11, namely the cutter head vent 13 can be directly closed by the first sealing member 43; and when the spring 42 is compressed by the pressure in the inner cavity 14, the first sealing member 43 is separated from the cutter head vent 13, such that the cutter head vent 13 is not closed.

In another implementation process, the first sealing member 43 is connected with the rear end face of the cutter head front section 11; the first side, along the radial direction of the cutter head structure 1, of the slider 41 is provided with a middle gap, it can be understood as that there is a middle gap formed in the side close to the axis shown in FIG. 2 and FIG. 3; the pressure relief intermediate cavity 3 includes a first pressure relief sub-cavity and a second pressure relief sub-cavity, wherein the first pressure relief sub-cavity is located on one side of the front end of the slider 41, and the second pressure relief sub-cavity is located on one side of the rear end of the slider 41. It can be understood as that the pressure relief intermediate cavity 3 is divided into sub-cavities on the two end sides in the axial direction.

When the first sealing member 43 is clamped by the slider 41 and the rear end face of the cutter head front section 11, the front end of the middle gap can also be closed by the first sealing member 43, such that the first pressure relief sub-cavity is isolated from the second pressure relief sub-cavity; and at the moment, the first pressure relief sub-cavity is considered as a space between the cutter head vent 13 and the front end of the slider 41 and can communicate with the cutter head vent 13 to form a whole body isolated from the second pressure relief sub-cavity.

When the spring 42 is compressed by the pressure in the inner cavity 14, the cutter head 13, the first pressure relief sub-cavity, the middle gap, the second pressure relief sub-cavity, the liner vent 51, the flexible pipe vent 21 and the pressure relief gap 22 communicate with one another in sequence.

In one example, the second side, along the radial direction of the cutter head structure 1, of the slider 41 is provided with a second sealing member 44, and the second sealing member 44 is configured to isolate the first pressure relief sub-cavity from the second pressure relief sub-cavity on the second side of the slider 41. The second side refers to a second side in the radial direction.

In a further example, the second side of the slider 41 may be provided with a groove, and the second sealing member 44 may be installed in the groove.

In a specific implementation process, the first sealing member 43 and the second sealing member 44 may be sealing rings.

In a further example, the slider 41 is pushed forwards by a thrust of the spring 42, and based on the sealing of the two sealing rings, a gas in the cutter head front section 11 is prevented from entering the pressure relief gap 22. If the return gas is blocked, an internal pressure of the cutter head structure 1 rises; and if the pressure of the gas is higher than the thrust provided by the spring 42, the slider 41 is enabled to slide backwards, and the gas enters the pressure relief gap 22 via the cutter head vent 13 and the pressure relief intermediate cavity 3. Excessive gas can be exhausted quickly by vacuum suction generated by an assembly such as a pumping assembly so as to relieve the pressure.

During specific use, the cutter head rear section 12 can be sequentially sheathed with a first sealing member 43 such as a sealing ring, a slider 41 provided with a sealing ring 2, a spring 42, and a partition plate which is located between the cutter head front section 11 and the cutter head rear section 12, namely the rear end face of the cutter head front section 11 is provided with four cutter head vents 13 in the axial direction for ventilation during pressure relief; the first sealing member 43 such as a sealing ring is configured to realize axial sealing between the cutter head rear section 12 and the slider 41; the second sealing member 44 such as a sealing ring is configured to realize radial piston sealing between the liner pipe 5 and the slider 41; there is a certain gap between the inner side of the slider 41 and the outer side of the cutter head rear section 12, namely the aforementioned middle gap, which is for ventilation during pressure relief; type selection of the spring 42 shall consider an expected to-be-relieved pressure $P_{relief}$, a maximum bore pressure $P_{catheter}$ of the flexible inner catheter 23 in the flexible pipe structure, a maximum normal back pressure $P_{back}$ in the cutter head structure 1, and a minimum vacuum pressure $P_{vacuum}$ (all are absolute pressures), wherein a reference formula is: $P_{catheter} > P_{relief} > (P_{back} - P_{vacuum})$.

The liner pipe 5 sleeves the cutter head rear section 12. There are two welding points 54 at contact positions of the two ends of the liner pipe 5 and the cutter head rear section 12. The welding point 54 at the front end enables a gas in the cutter head structure 1 not to be leaked out of the cutter head structure 1; and the welding point 54 at the rear end enables a gas in the flexible inner catheter 23 not to enter the pressure relief gap 22.

In the related existing art, in order to realize automatic pressure relief, a general idea is to realize it by combination of a pressure sensor and a solenoid valve. The present disclosure can also use this implementation mode; also, under a specific condition that the space is limited, the above implementation mode creatively use the motion modes of the slider, the sealing members and the spring for reference for a flexible cryoscalpel, and thus automatic pressure relief is realized with a simpler structure, a lower cost and less space use.

It can be seen that gas is sucked and exhausted by the spring 42, the sealing rings and the pressure relief gap 22, and thus the air tightness under a normal working state is guaranteed by a compressive force of the spring 42 and the sealing rings. When the pressure is extremely high, gas is exhausted through compression of the spring, and can be quickly exhausted out of a product through suction of the pressure relief gap 22.

The flexible cryoablation needle device related to the present disclosure further includes a liner pipe 5; the front end of the liner pipe 5 is connected with the rear end surface of the cutter head front section 11; the pressure relief intermediate cavity 3 is formed between the inner side of the liner pipe 5 and the outer side of the cutter head rear section 12 and along the radial direction of the cutter head structure 1; the liner pipe 5 is provided with a liner vent 51; the pressure relief intermediate cavity 3 communicates with the pressure relief gap 22 through the liner vent 51 and the flexible pipe vent 21; the flexible pipe structure 2 is arranged on the outer side of the liner pipe 5 along the radial direction of the cutter head structure 1; and at least a part of the outer wall of the liner pipe 5 is attached to the inner wall of the flexible pipe structure 2. The liner pipe 5 can facilitate the formation of the pressure relief intermediate cavity 3.

Wherein, the outer wall, attached to the flexible pipe structure 2, of the liner pipe 5 may be provided with a concave-convex structure, and the concave-convex structure may include a threaded part 52. The threaded portion 52 can enhance the connection strength of the liner pipe and the flexible pipe structure. The concave-convex structure may further include an annular protrusion portion 53, namely the outer wall, attached to the flexible pipe structure 2, of the liner pipe 5 may further be provided with an annular protrusion portion 53. The annular protrusion portion 53 can prevent further leakage of a gas coming from a pressure relief process and can enhance the connection strength as well. In a specific example, there may be two groups of annular protrusion portions 53, which are located on the two sides of the liner vent 51 along the axial direction of the cutter head structure 1, respectively.

The flexible cryoablation needle device related to the present disclosure further includes a first extruding pipe 6, and the first extruding pipe 6 is sleeved outside the flexible pipe structure 2 and is located on the outer side of the concave-convex structure. Specifically, the concave-convex structure may include, for example, an annular protrusion portion 53 and a threaded part 52.

In one example, the flexible cryoablation needle device may further include a second extruding pipe 8 which sleeves the inner wall of the pressure relief gap 22, namely the second extruding pipe 8 is sleeved outside the flexible inner catheter 23 in the flexible pipe structure 2 and is located on the outer side of the concave-convex structure. Specifically, the concave-convex structure may include, for example, an annular protrusion portion 53.

It can be seen that the air tightness and connection strength are further guaranteed by radial extrusion of the extruding pipes. As shown in the figures, the extruding pipe outside the flexible pipe structure 2 may be the first extruding pipe 6, and the extruding pipe at the inner wall of the pressure relief gap 22 may be the second extruding pipe 8. The first extruding pipe 6 and the second extruding pipe 8 are located on the two sides of the liner vent 51 and the flexible pipe vent 21 along the axial direction of the cutter head structure 1, respectively.

It can be seen that the above example can meet the requirements of both a high pressure resistance and a low temperature resistance based on the mode of connection between a plastic flexible pipe structure 2 and a metal cutter head structure 1.

In one example, the flexible pipe structure 2 includes a flexible inner catheter 23 and a flexible outer catheter 24 which is arranged outside the flexible inner catheter 23; the flexible outer catheter 24 includes a first outer catheter section 241 and a second outer catheter section 242, wherein the first outer catheter section 241 is connected to the cutter head structure 1; the second outer catheter section 242 is connected to the rear end of the first outer catheter section 241; the inner wall of the first outer catheter section 241 is attached to the outer wall of the flexible inner catheter 23; the pressure relief gap 22 is formed between the second outer catheter section 242 and the flexible inner catheter 23; the flexible pipe vent 21 is formed in the flexible inner catheter 23; and the pressure relief gap 22 communicates with a pumping assembly.

Wherein the flexible inner catheter 23 and the flexible outer catheter 24 may be made from poly tetra fluoroethylene. A poly tetra fluoroethylene catheter has a desired toughness even at a low temperature.

In the above example, a threaded part and an annular protrusion portion, as well as extrusion between a metal cutter head structure and a poly tetra fluoroethylene catheter are adopted, wherein the threaded part provides a connection strength, the annular protrusion portion guarantees the air tightness, the extrusion between the metal cutter head structure and the poly tetra fluoroethylene catheter further enhances the connection strength and the air tightness, and the toughness is improved as well.

In a specific example, the flexible pipe structure 2 is screwed into the threaded part 52, and the teeth of the threaded part 52 in the radial direction will be embedded in the wall of the flexible pipe structure 2. Wherein, the wall thickness of the flexible inner catheter 23 in the flexible pipe structure 2 is at least not less than 2 times the tooth height, such that the too bit structure 1 and the flexible pipe structure 2 can be prevented from separation from each other due to an axial pressure; moreover, the axial pressure can be dispersed to each circle of teeth due to embedding of a plurality of circles of teeth; however, the flexible pipe structure 2 also tends to expand outwards in the radial direction, therefore except the embedding of the teeth, the outer side of the flexible pipe structure 2 is further additionally provided with an extruding pipe for extrusion, such that outward expansion of the flexible inner catheter 23 in the flexible pipe structure 2 can be prevented, and the teeth and the flexible pipe structure 2 are combined in an embedding manner and make contact with each other fully. Therefore, the solution of combination of the threaded part and the extruding pipe can also guarantee a sufficient compression strength of the cutter head structure 1.

The annular protrusion portion 53, with the extrusion of the extruding pipe, guarantees that a gas coming from a pressure relief process cannot be leaked out of the cutter head structure 1, also provides a certain axial connection strength, and guarantees that a gas in the flexible pipe catheter 23 cannot enter the pressure relief gap 22.

The gas in the flexible inner catheter 23 can also be prevented from leaking out of the cutter head structure 23 by coaction of the two groups of annular protrusion portions.

In most of high-temperature sealed places, a rubber material with a certain elasticity is adopted to achieve a sealing function through its deformation and extrusion in a hard sealing groove. Since a cutter head structure 1 of a flexible cryoscalpel is generally in a working environment at a low temperature as low as −170° C., most of rubber or plastic materials will be embrittled at such a low temperature, resulting in ineffective sealing. In this example, since the poly tetra fluoroethylene material adopted has a good mechanical toughness, it can maintain an elongation of 5% even when the temperature drops to −196° C. Therefore, poly tetra fluoroethylene is adopted to manufacture the flexible inner catheter 23 and the flexible outer catheter 24. Moreover, with extrusion of the two groups of annular protrusion portions and extruding pipes, safe sealing under a low temperature can be realized.

The flexible inner catheter 23 and the flexible outer catheter 24 prevents a gas outside the cutter head structure 1 from being sucked into the pressure relief gap 22 by extrusion of the extruding pipes. The flexible inner catheter 23 is provided with an inner catheter gas hole part in the radial direction; the flexible outer catheter 24 is provided with an outer catheter gas hole part in the radial direction; and the inner catheter gas hole part and the outer catheter gas hole part can be concentrically aligned and combined to form the above-mentioned flexible pipe vent.

Compared with the present disclosure, the methods adopting threaded connection for sealing or adopting threaded connection and glue connection for sealing and the like are low in air tightness due to use of threaded sealing (especially pipe threads), and a small amount of gas will be leaked via a matching gap of male threads and female threads. Therefore, these methods cannot meet the requirements of a low temperature resistance and a high pressure resistance. Since most of glue will be embrittled under a low temperature of −140° C. to −170° C. and accordingly cannot guarantee the air tightness, even the filling of thread glue in the gap can only guarantee an air tightness under a normal temperature or an appropriate low temperature.

In one example, the flexible cryoablation needle device further includes a pipeline structure 7; the pipeline structure 7 penetrates into the cutter head rear section 12 along the axial direction of the cutter head structure 1; an entry channel for a gas to enter the inner cavity is formed in the pipeline structure 7; and the pipeline structure 7 may be, for example, a Joule-Thomson (J-T) groove. A gas return channel for a gas in the inner cavity to be exhausted to one side of the rear end of the liner pipe 5 is formed between the inner side of the cutter head rear section 12 and the outer side of the pipeline structure 7.

It can be seen that a gas can enter the inner cavity 14 of the cutter head front section 11 from the inner side of the pipeline structure 7 which is, for example, a J-T groove; subsequently, the gas returns via a gap, namely the above-mentioned gas return channel, between the cutter head rear section 12 and the outer side of the pipeline structure 7 which is, for example, a J-T groove; and then the gas returns through the inner side of the flexible inner catheter 23.

In conclusion, in the flexible cryoablation needle device resistant to a low temperature and a high pressure provided by the present disclosure, the threaded part arranged on the outer wall of the liner pipe can enhance the connection strength of the liner pipe and the flexible pipe structure, and the annular protrusion portions arranged on the outer wall of the liner pipe guarantee that a gas coming from a pressure relief process cannot be further leaked outwards and also enhance the connection strength. Also, the flexible cryoablation needle device provided by the present disclosure can further guarantee the air tightness and the connection strength by radial extrusion of the extruding pipes.

Also, according to the flexible cryoablation needle device provided by the present disclosure, the inner cavity in the cutter head is directly subjected to pressure relief through the cutter head vent, the pressure relief intermediate cavity, the liner vent, the flexible pipe vent and the pressure relief gap, wherein when a pressure in the inner cavity is higher than or equal to a pressure threshold, pressure relief can be automatically controlled to avoid occurrence of an extremely high pressure in the cutter head, thereby avoiding burst of a catheter.

The present disclosure is also different from a solution of directly arranging pressure relief related members in a gas return channel. If the pressure relief related members are directly arranged in the gas return channel, automatic pressure relief is only realized when the gas return channel is blocked. If a gas return channel of a flexible cryoscalpel is blocked, a positive pressure relief function cannot be achieved. However, based on actual experiments and studies on blocking phenomena during use, it is found in the present disclosure that in actual situations, blocking may occur at any other position, such as a flexible catheter of a flexible cryoscalpel, an extension pipe section, etc.; therefore, the present disclosure realizes direct pressure relief of a cutter head, thereby effectively responding to a variety of blocking conditions and conveniently responding to a situation about an extremely high pressure in a cutter head caused by various reasons.

In the related existing art, in order to realize automatic pressure relief, a general idea is to realize automatic pressure relief through the combination of a pressure sensor and a solenoid valve. In an optional solution of the present disclosure, under a specific condition that the space is limited, a flexible cryoscalpel uses the motion modes of the slider, the sealing members and the spring for reference, and thus automatic pressure is realized with a simpler structure, a lower cost and less space use.

In an optional solution of the present disclosure, a double-layered pipe structure including a flexible inner catheter and a flexible outer catheter is used to facilitate heat insulation and prevent injuries of a human body caused by a low temperature of a flexible cryoscalpel. Also, a heat insulation effect can be further improved during pressure relief by generation of a pressure relief gap and/or vacuumizing of the pressure relief gap.

In addition, in view of the situation that a rubber or plastic material in the related existing art will be embrittled at a low temperature, an optional solution of the present disclosure uses a tetra fluoroethylene material. With a good mechanical toughness, a tetra fluoroethylene material can maintain an elongation of 5% even when a temperature drops to −196° C. Therefore, safe sealing under a low temperature can be realized by adopting tetra fluoroethylene for manufacturing inner and outer layers of flexible catheters.

In the end, it should be noted that the above examples are merely intended to describe technical solutions of the present invention rather than to limit them; although the present invention has been described in detail with reference to the foregoing examples, those of ordinary skill in the art should understand that: it is still possible to modify the technical solutions described in the foregoing examples, or equivalently substitute some or all of technical features; and these modifications or substitutions do not make the nature of the corresponding technical solutions depart from the scope of the technical solutions of the examples of the present invention.

What is claimed is:

1. A flexible cryoablation needle device resistant to a low temperature and a high pressure, comprising: a cutter head structure and a flexible pipe structure connected to the rear end of the cutter head structure, the cutter head structure is provided with an inner cavity, and the cutter head structure comprises a cutter head front section and a cutter head rear section; the front end of the cutter head rear section is connected to the rear end of the cutter head front section; the cutter head rear section has a smaller outer diameter than the cutter head front section; wherein the flexible cryoablation needle device further comprises a liner pipe, a pressure relief assembly, a pressure relief intermediate cavity and a first extruding pipe; the flexible pipe structure is provided with a pressure relief gap and a flexible pipe vent; the rear end face of the cutter head front section is provided with a cutter head vent; the liner pipe is provided with a liner vent;

the front end of the liner pipe is connected with the rear end face of the cutter head front section; the pressure relief intermediate cavity is formed between the inner side of the liner pipe and the outer side of the cutter head rear section along the radial direction of the cutter head structure; the pressure relief intermediate cavity is formed between the rear end face of the cutter head front section and a fixing part along the axial direction of the cutter head structure; the fixing part is connected between the outer side of the cutter head rear section and the inner side of the liner pipe; the flexible pipe structure is arranged on the outer side of the liner pipe along the radial direction of the cutter head structure; the pressure relief intermediate cavity communicates with the pressure relief gap through the liner vent and the flexible pipe vent; the inner cavity is connected to one side of the cutter head vent; the pressure relief intermediate cavity is connected to the other side of the cutter head vent;

at least a part of the outer wall of the liner pipe is attached to the inner wall of the flexible pipe structure; the outer wall, attached to the flexible pipe structure, of the liner pipe is provided with a concave-convex structure; the first extruding pipe is sleeved outside the flexible pipe structure and is located on the outer side of a part of the concave-convex structure; the concave-convex structure comprises a threaded portion and an annular protrusion portion; and the pressure relief assembly is arranged in the pressure relief intermediate cavity to close the cutter head vent when a pressure in the inner cavity is lower than a pressure threshold, and control the cutter head vent, the flexible pipe vent and the liner vent to communicate with one another when the pressure in the inner cavity is higher than or equal to the pressure threshold, such that a gas in the cutter head structure is exhausted to relieve the pressure through the cutter head vent, the pressure relief intermediate cavity, the liner vent, the flexible pipe vent and the pressure relief gap in sequence.

2. The flexible cryoablation needle device according to claim 1, wherein the pressure relief assembly comprises a slider and a spring which are located in the pressure relief intermediate cavity; the spring is connected with the slider and the fixing part along the axial direction of the cutter head structure; a first sealing member is arranged on one side of the rear end face of the cutter head front section; and the spring is configured to cause the first sealing member to be driven by an elastic force and clamped by the slider and the rear end face of the cutter head front section when a pressure in the inner cavity is lower than a pressure threshold so as to close the cutter head vent; and the spring is compressed by the pressure in the inner cavity when the pressure in the inner cavity is higher than or equal to the pressure threshold, such that the cutter head vent is not closed.

3. The flexible cryoablation needle device according to claim 2, wherein the first sealing member is connected with the front end of the slider; the cutter head vent is closed by the first sealing member when the first sealing member is clamped by the slider and the rear end face of the cutter head front section; and when the spring is compressed by the pressure in the inner cavity, the first sealing member is separated from the cutter head vent, such that the cutter head vent is not closed.

4. The flexible cryoablation needle device according to claim 2, wherein the first sealing member is connected with the rear end face of the cutter head front section; the first side, along the radial direction of the cutter head structure, of the slider is provided with a middle gap; the pressure relief intermediate cavity comprises a first pressure relief sub-cavity and a second pressure relief sub-cavity, wherein the first pressure relief sub-cavity is located on one side of the front end of the slider, and the second pressure relief sub-cavity is located on one side of the rear end of the slider;

the front end of the middle gap is closed by the first sealing member when the first sealing member is clamped by the slider and the rear end face of the cutter head front section, such that the first pressure relief sub-cavity is isolated from the second pressure relief sub-cavity; and when the spring is compressed by the pressure in the inner cavity, the cutter head vent, the first pressure relief sub-cavity, the middle gap, the second pressure relief sub-cavity, the flexible pipe vent and the pressure relief gap communicate with one another in sequence.

5. The flexible cryoablation needle device according to claim 4, wherein the second side, along the radial direction of the cutter head structure, of the slider is provided with a second sealing member; and the second sealing member is configured to isolate the first pressure relief sub-cavity from the second pressure relief sub-cavity on the second side of the slider.

6. The flexible cryoablation needle device according to claim 5, wherein the second side of the slider is provided with a groove, and the second sealing member is installed in the groove.

7. The flexible cryoablation needle device according to claim 1, wherein the flexible pipe structure comprises a flexible inner catheter and a flexible outer catheter which is arranged outside the flexible inner catheter; the flexible outer catheter comprises a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

8. The flexible cryoablation needle device according to claim 7, wherein the material of the flexible inner catheter and the flexible outer catheter is poly tetra fluoroethylene.

9. The flexible cryoablation needle device according to claim 7, further comprising a second extruding pipe, wherein the second extruding pipe is sleeved outside the flexible inner catheter and is located on the outer side of part of the concave-convex structure.

10. The flexible cryoablation needle device according to claim 1, further comprising a pipeline structure, wherein the pipeline structure penetrates into the rear section of the cutter head along the axial direction of the cutter head structure; an entry channel is arranged in the pipeline structure to allow air to enter the inner cavity; and a gas return channel is formed between the inner side of the cutter head rear section and the outer side of a channel structure to allow the air in the inner cavity to exhaust to one side of the rear end of the cutter head rear section.

11. The flexible cryoablation needle device according to claim 2, wherein the flexible pipe structure comprises a flexible inner catheter and a flexible outer catheter which is arranged outside the flexible inner catheter; the flexible outer catheter comprises a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

12. The flexible cryoablation needle device according to claim 3, wherein the flexible pipe structure comprises a flexible inner catheter and a flexible outer catheter which is arranged outside the flexible inner catheter; the flexible outer catheter comprises a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

13. The flexible cryoablation needle device according to claim 4, wherein the flexible pipe structure comprises a flexible inner catheter and a flexible outer catheter which is arranged outside the flexible inner catheter; the flexible outer catheter comprises a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

14. The flexible cryoablation needle device according to claim 5, wherein the flexible pipe structure comprises a flexible inner catheter and a flexible outer catheter which is arranged outside the flexible inner catheter; the flexible outer catheter comprises a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

15. The flexible cryoablation needle device according to claim 6, wherein the flexible pipe structure comprises a flexible inner catheter and a flexible outer catheter which is arranged outside the flexible inner catheter; the flexible outer catheter comprises a first outer catheter section and a second outer catheter section, wherein the first outer catheter section is connected to the cutter head structure; the second outer catheter section is connected to the rear end of the first outer catheter section; the inner wall of the first outer catheter section is attached to the outer wall of the flexible inner catheter; the pressure relief gap is formed between the second outer catheter section and the flexible inner catheter; the flexible pipe vent is formed in the flexible inner catheter; and the pressure relief gap communicates with a pumping assembly.

16. The flexible cryoablation needle device according to claim 2, further comprising a pipeline structure, wherein the pipeline structure penetrates into the rear section of the cutter head along the axial direction of the cutter head structure; an entry channel is arranged in the pipeline structure to allow air to enter the inner cavity; and a gas return channel is formed between the inner side of the cutter head rear section and the outer side of a channel structure to allow the air in the inner cavity to exhaust to one side of the rear end of the cutter head rear section.

17. The flexible cryoablation needle device according to claim 3, further comprising a pipeline structure, wherein the pipeline structure penetrates into the rear section of the cutter head along the axial direction of the cutter head structure; an entry channel is arranged in the pipeline structure to allow air to enter the inner cavity; and a gas return channel is formed between the inner side of the cutter head rear section and the outer side of a channel structure to allow the air in the inner cavity to exhaust to one side of the rear end of the cutter head rear section.

18. The flexible cryoablation needle device according to claim 4, further comprising a pipeline structure, wherein the pipeline structure penetrates into the rear section of the cutter head along the axial direction of the cutter head structure; an entry channel is arranged in the pipeline structure to allow air to enter the inner cavity; and a gas return channel is formed between the inner side of the cutter head rear section and the outer side of a channel structure to allow the air in the inner cavity to exhaust to one side of the rear end of the cutter head rear section.

19. The flexible cryoablation needle device according to claim 5, further comprising a pipeline structure, wherein the pipeline structure penetrates into the rear section of the cutter head along the axial direction of the cutter head structure; an entry channel is arranged in the pipeline structure to allow air to enter the inner cavity; and a gas return channel is formed between the inner side of the cutter head rear section and the outer side of a channel structure to allow the air in the inner cavity to exhaust to one side of the rear end of the cutter head rear section.

20. The flexible cryoablation needle device according to claim 6, further comprising a pipeline structure, wherein the pipeline structure penetrates into the rear section of the cutter head along the axial direction of the cutter head structure; an entry channel is arranged in the pipeline structure to allow air to enter the inner cavity; and a gas return channel is formed between the inner side of the cutter head rear section and the outer side of a channel structure to allow the air in the inner cavity to exhaust to one side of the rear end of the cutter head rear section.

\* \* \* \* \*